United States Patent
Thorn

(10) Patent No.: US 6,395,039 B1
(45) Date of Patent: *May 28, 2002

(54) PROSTHETIC SUSPENSION UNIT INCLUDING AN ELASTOMERIC ENERGY STORAGE ELEMENT

(75) Inventor: Richard P. Thorn, Erie, PA (US)

(73) Assignee: Lord Corporation, Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/373,435

(22) Filed: Aug. 11, 1999

Related U.S. Application Data

(63) Continuation of application No. 08/775,544, filed on Dec. 31, 1996, now Pat. No. 5,961,556.

(51) Int. Cl.$^7$ .................................................. A61F 2/80
(52) U.S. Cl. ............................................. 623/35; 623/44
(58) Field of Search .............................. 623/27, 28, 32, 623/35, 44; 248/406.2, 575

(56) References Cited

U.S. PATENT DOCUMENTS

| | | |
|---|---|---|
| 622,140 A | 3/1899 | Ginn |
| 2,559,446 A | 7/1951 | Lucas et al. ........................ 3/2 |
| 3,842,443 A | 10/1974 | Weber ................................ 3/2 |
| 3,851,337 A | 12/1974 | Prahl ................................ 3/32 |
| 4,038,705 A | 8/1977 | Owens et al. ....................... 3/2 |
| 4,134,159 A | 1/1979 | Wilson ............................... 3/2 |
| 4,446,580 A | 5/1984 | Furuya et al. ...................... 3/6 |
| 4,883,493 A | 11/1989 | Martel et al. .................. 623/38 |
| 5,133,777 A | 7/1992 | Arbogast et al. ............... 623/38 |
| 5,217,500 A | 6/1993 | Phillips ........................ 623/38 |
| 5,405,407 A | 4/1995 | Kodama et al. ................ 623/44 |
| 5,443,521 A | 8/1995 | Knoth et al. ................... 623/44 |
| 5,458,656 A | 10/1995 | Phillips ........................ 623/27 |
| 5,511,759 A * | 4/1996 | DeKracker et al. ......... 248/575 |
| 5,702,488 A | 12/1997 | Wood et al. ................... 623/27 |
| 5,800,563 A | 9/1998 | Arbogast et al. ............. 623/35 |
| 5,888,214 A * | 3/1999 | Ochoa .......................... 623/27 |
| 5,961,556 A * | 10/1999 | Thorn .......................... 623/27 |
| 6,086,615 A * | 7/2000 | Wood et al. ................... 623/27 |
| 6,214,056 B1 * | 4/2001 | Wilkerson .................... 623/35 |

FOREIGN PATENT DOCUMENTS

| | | |
|---|---|---|
| DE | 327494 | 10/1920 |
| DE | 295 16 455 U1 | 3/1996 |
| FR | 587.591 | 1/1925 |
| GB | 2014 855 A | 9/1979 |
| WO | WO 93/24080 | 12/1993 |

* cited by examiner

Primary Examiner—Paul B. Prebilic
(74) Attorney, Agent, or Firm—Michael M. Gnibus; Randall S. Wayland

(57) ABSTRACT

A prosthetic suspension unit for cushioning shocks in amputees is provided. The prosthetic suspension unit has a first member adapted to be secured to a first prosthetic member and a stop located in the first member. An attachment member is adapted to be secured to a second prosthetic member. A bearing member is operative between the attachment member and the first member such that the attachment member may slide freely in an axial direction relative to the first member. An elastomeric energy storage element is positioned within the first member and includes a first portion abutting the stop. A second portion abuts a face axially moveable with the attachment member to compress the storage member upon application of load by the user.

18 Claims, 3 Drawing Sheets

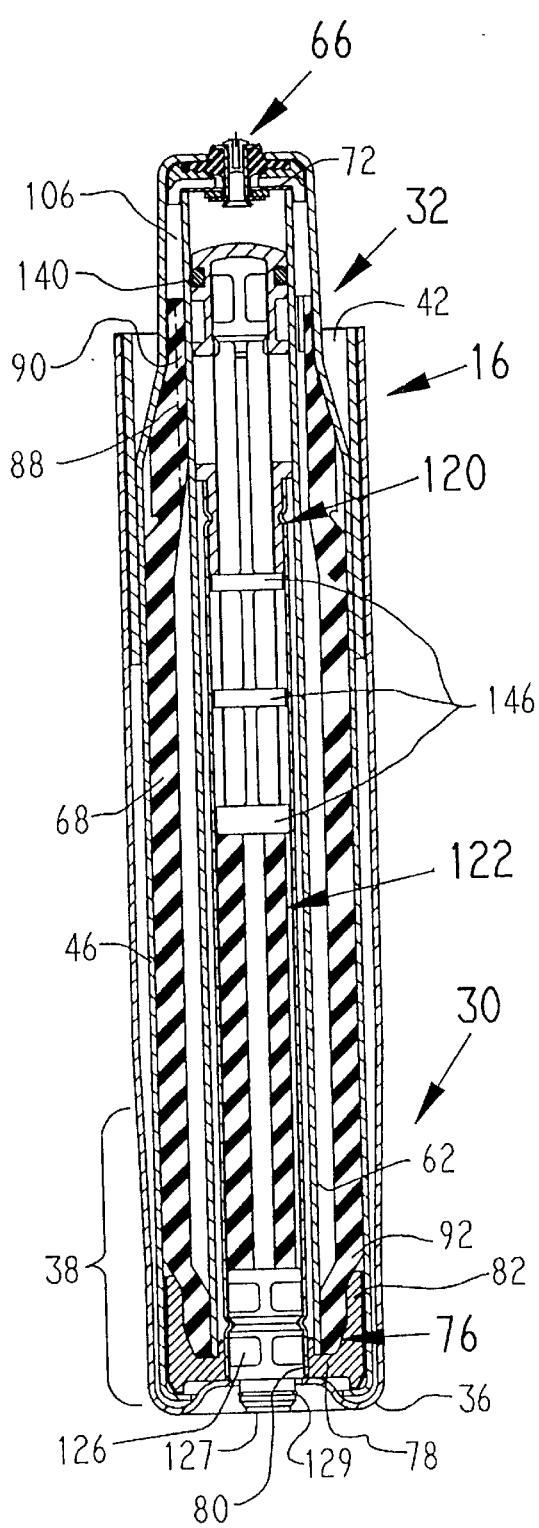
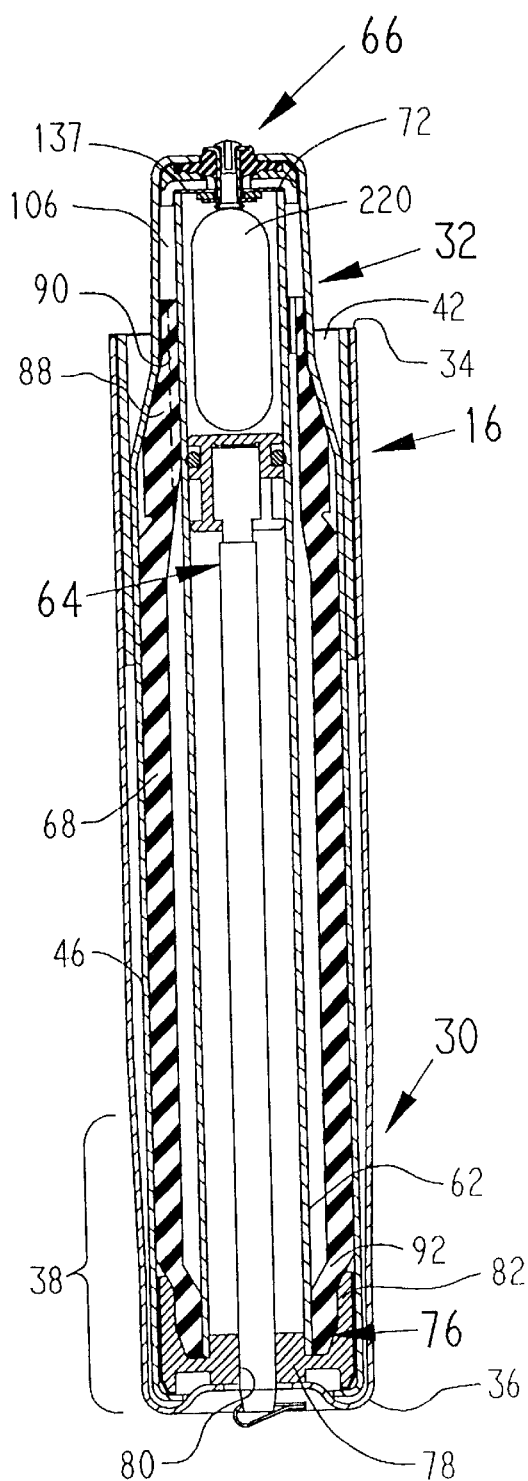
FIG. 1A
FIG. 1B
(PRIOR ART)

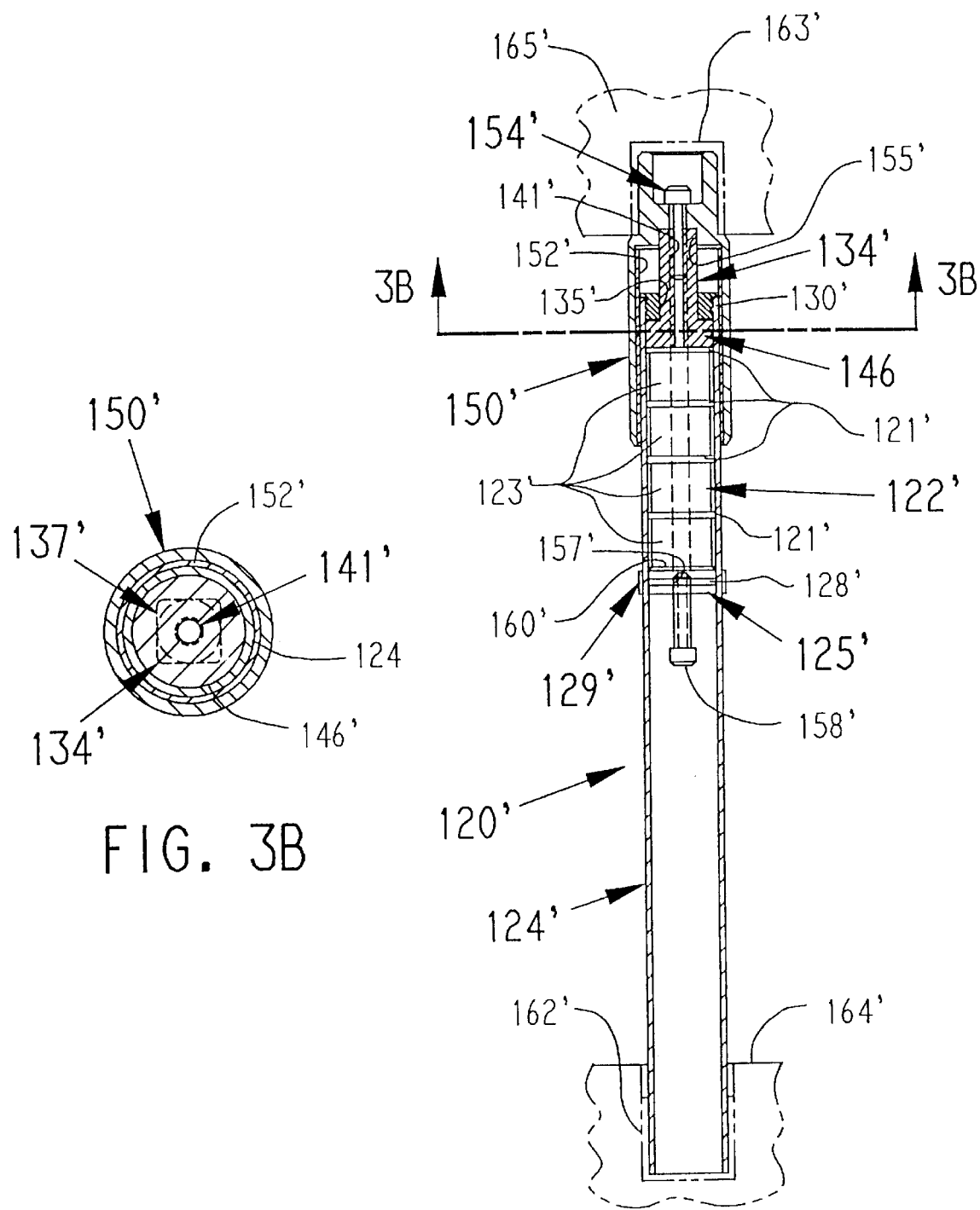

US 6,395,039 B1

PROSTHETIC SUSPENSION UNIT INCLUDING AN ELASTOMERIC ENERGY STORAGE ELEMENT

RELATED APPLICATIONS

This is a Continuation Application of U.S. patent application Ser. No. 08/775,544 filed Dec. 31, 1996 now U.S. Pat. No. 5,961,556.

BACKGROUND AND SUMMARY OF THE INVENTION

This invention is directed to a linear energy management unit or cush. More particularly, the present invention is directed to an energy management unit having a long stroke. This cush is an improvement over that which is described and claimed in U.S. Pat. No. 5,511,759 entitled "Hydraulic Chair Height Adjustment Mechanism" in which the assignee of the present invention has an interest, which is hereby incorporated by reference.

In the above cited patent, a closed-cell microcellular urethane foam member which is coated with a fluid-impervious urethane material is placed in the fluid compartment of a seat height adjustment device. An elastomeric bladder is used to store energy and to raise the seat to a fully extended position from which adjustment can be made. The hydraulic fluid used in the adjustment mechanism is incompressible and would provide anyone sitting in the chair a jolt or shock. The purpose of the cush is to provide a softer feel, to effectively cushion the system such that when a person is first seated in the chair, the incompressible fluid can compress something other than his or her backside.

There are several problems with this type of cush. Firstly, it is limited in its ability to effectively cushion a load, i.e., it has a short stroke. Secondly, there is no possibility to preload the cush. This is important as adjustable height chairs are brought into regulatory compliance. Current test standards require that the chair be able to have adjustability over a given stroke length when loaded with a weight of 130 lbs. Without the benefit of a preload, the seat will sag under load and additional stroke length will need to be afforded resulting in added component length and added expense. Thirdly, repeated cycling in the fluid environment results in some of the cells of the cush collapsing further reducing the cushioning effectiveness of the device.

In order to make the energy management unit more effective, as well as more versatile, i.e., capable of use in other applications, a significant re-thinking of the cush was necessary. The preferred embodiments of the present design provide an energy management unit that is a self-contained capsule which can simply be inserted into the system with which it is used. The elastomeric portions of the cush are isolated from the hydraulic fluid of the host system so that costly coatings can be avoided. Further, the present cush design is a linear device with an extended stroke to provide significantly greater cushioning than was previously possible.

A relatively unstable, collapsible elastomeric member is provided with guide means throughout its length (either circumferential or longitudinal). This elastomeric member is confined within a cylindrical sleeve to stabilize its movement. One end of the sleeve is plugged and the other end is provided with a slidable piston. The elastomeric member may be precompressed a desired amount (for the seat height adjuster application, by an amount sufficient to offset the 130 lb. weight). A protruding piston head can be provided with an O-ring to provide a sealing engagement with an inner cylinder which houses the capsulized cush to isolate the elastomeric member from the working fluid. The guide means engages the internal surface of the guide tube and provides damping of movement between the piston and the guide tube. A second embodiment for non-fluid applications is also provided. Adjustment capability for the precompression of the elastomeric means can be provided for appropriate applications.

Other features, advantages and characteristics of the present invention will become apparent after a reading of the following detailed description of the preferred embodiments.

BRIEF DESCRIPTION OF THE DRAWINGS

The following figures depict the preferred embodiments of the present invention, like items bearing like reference numerals and, in which FIG. 1A is a partial cross-sectional side view of a first embodiment of the energy management unit of the present invention in a seat height adjuster;

FIG. 1B is a partial cross-sectional side view of a prior art seat height adjuster with the cush the present invention is designed to replace;

FIG. 3A is a cross-sectional side view of a third embodiment of the energy management unit of the present invention for a different application; and FIG. 3B is an end view of the piston used in this third embodiment.

DETAILED DESCRIPTION OF THE PREFERRED EMBODIMENTS

Figure 1C:
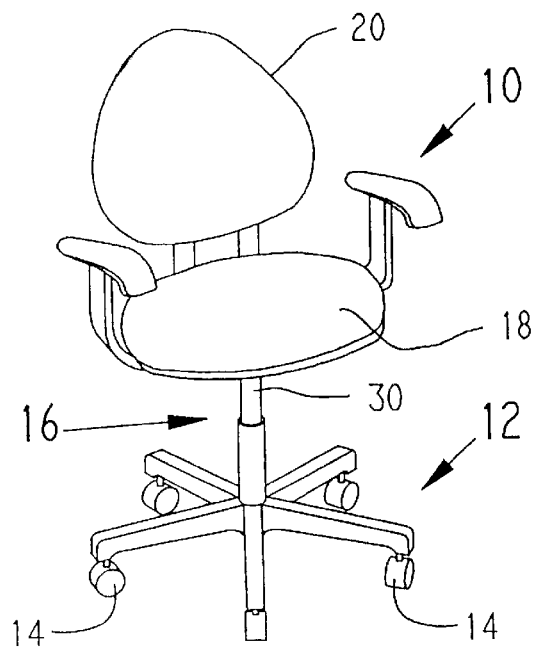
FIG. 1C is an adjustable seat height chair in which the present invention can be used.
Figure 2B:
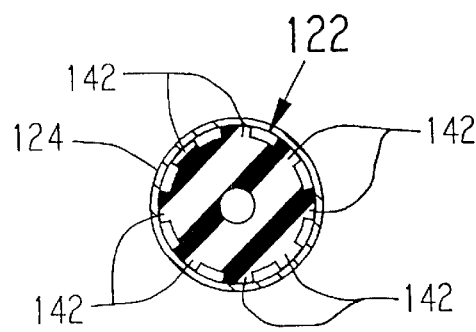
FIG. 2B is an end view of one embodiment of the energy storage device of the present invention.
Figure 2C:
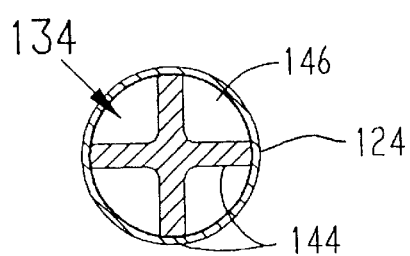
FIG. 2C is a cross-sectional end view of the piston rod taken along line 2C—2C in FIG. 2A.
Figure 2A:
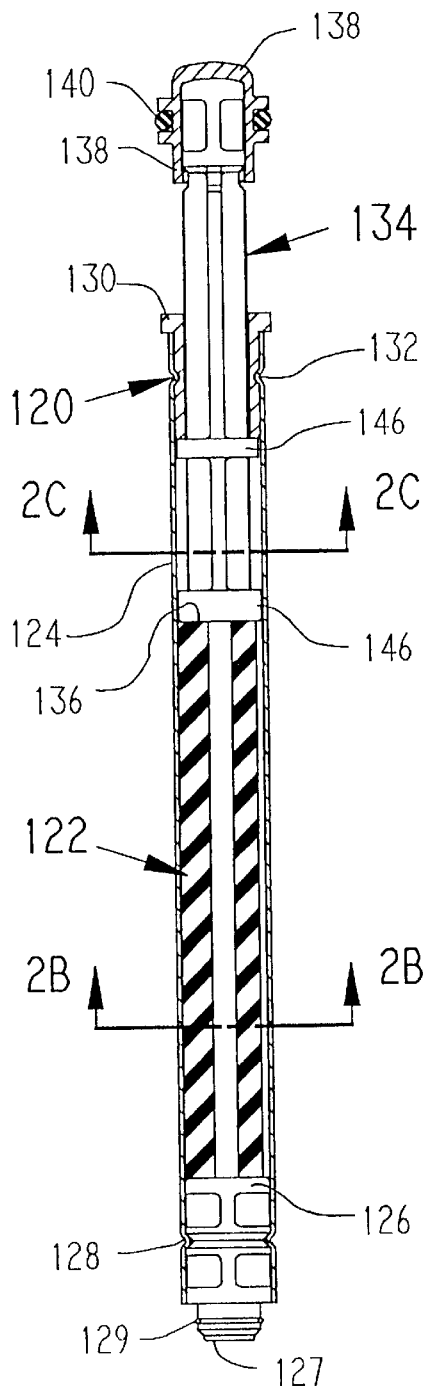
FIG. 2A is a partial cross-sectional side view of a second embodiment of the energy management unit of the present invention.

A first embodiment of the energy management unit of the present invention is shown in FIGS. 1A, with a slight variation shown in FIG. 2A, generally at 120. FIG. 2A shows the cush 120 itself while FIG. 1A depicts it in use in a seat height adjuster 16. As seen in FIG. 1C, chair 10 includes a pedestal 12 which is supported on casters 14. Seat height adjustment mechanism 16 is housed in support tube 30, while chair 10 is provided with a cushioned seat 18 and seat back 20. Cush 120 will be described in conjunction with FIG. 2A.

Cush 120 includes relatively unstable, collapsible elastomeric means 122 which is contained within cylindrical sleeve 124. Cylindrical sleeve 124 provides elastomeric means 122 with controlled, stable deflection. One end of sleeve 124 is closed by plug 126 which is secured in place by crimping sleeve 124 as at 128. The opposite end of sleeve 124 is closed by a cylindrical collar 130 which is similarly held in place by crimping sleeve 124 as, at 132. A first end of piston rod 134 extends through collar 130 and engages an upper end 136 of elastomeric means 122. A second end of piston rod 134 has a piston head 138 formed thereon with an O-ring 140 extending thereabout for sealingly engaging an inner cylinder 62.

As best seen in FIG. 2B, elastomeric means 122 is provided with guide means in the form of longitudinal ribs 142 running the length of the elastomeric means 122. The radially outermost surface of guide means 142 will be provided with a lubricant to reduce wear. The collapse of elastomeric means 122 into contact with the inner surface of sleeve 124 will produce damping to relative motion between piston rod 134 and cylindrical sleeve 122. The elastomeric means 122 is preferably made of natural rubber, although other materials such as urethane and Hytrel plastics may be used, as well. The durometer of the material in the elastomeric means 122 preferably falls in the range of between 50 and 80.

The piston rod 134 is preferably made of a rigid plastic material and of cruciform cross section as shown in FIG. 2C, the radially extending ribs 144 providing maximum strength for minimum material usage and weight. Plug 126 will be similarly shaped. At a plurality of locations along its length, radially extending flanges 146 are provided to stabilize the piston rod 134 against canting within the sleeve 122. Depending on the desired length of the piston rod 134, either two (FIG. 2A) or three (FIG. 1A) flanges 146 will generally prove sufficient.

As can be seen in each of FIGS. 1A and 2A, the distance between lowermost surface of piston rod 134 and uppermost surface of plug 126 is fixed by crimpings at 132 and 128, respectively. The amount of preload provided the system can be adjusted by controlling the length of elastomeric means 122. It will typically be desired, for the seating application, to provide a preload equal to between 10% and 50% of the ultimate load of the elastomeric means 122 by compressing the elastomer between 5% and 40% of its uncollapsed length. As has been mentioned, the preload is necessary to prevent the seat height adjuster 16 from sagging under the specified test load, currently 130 lbs.

Comparing FIGS. 1A and 1B, it can be seen that much remains the same in the seat height adjuster 16. An outer support tube 30 receives column tube subassembly 32 in its open end 34. Subassembly 32 can move freely within tube 30 as inner support tube 46 slides within self-lubricating bearing 42. A lower portion 38 of support tube 30 tapers inwardly toward bottom 36. Cylinder 62 houses piston rod assembly 64 and has an open upper end 72. Valve mechanism 66 is attached to the upper end of support tube 46 and seat washer 137 closes open upper end 72 of cylinder 62. Valve mechanism controls the flow of hydraulic fluid to and from inside cylinder 62 from and to space 106 and, subsequently, into expandable bladder 68 through openings 90 in upper end 88. By storing the hydraulic fluid in the expandable bladder 68, energy is saved to lift the chair to its fully extended position for subsequent re-adjustment. End cap 76 includes a hub portion 78, which has a throughbore 80, and a cylindrical skirt 82 which captures lower end 92 of bladder 68.

As can be seen by comparing FIGS. 1A and 1B, the cush 120 of the present invention replaces and performs the functions of both cush 220 and piston 64. Plug 126 has an extension 127 that includes an annular recess that receives a retaining ring 129 that engages the lower surface of bottom 36 so that cush 120 is secured to support tube 30 and moves therewith, just as piston 64 did in the previous device of U.S. Pat. No. 5,511,759. Valve 66 still controls the flow of fluid to and from inside cylinder 62 from and to inside bladder 68 through space 106. O-ring 140 seals the hydraulic fluid in space 106 out of cush 120 and, hence, protects elastomer 122 from contact with such fluid. In the cush 120 of the present invention, a reduced amount of hydraulic fluid is required and the fluid flow is shielded from possible interference from the internal cush.

A third embodiment of the cush of the present invention is shown in FIGS. 3A generally at 120'. Sleeve 124' is stopped at one end by plug 125', sleeve 124' being crimped at 128' to secure the plug 125' in the desired position. Sleeve 124' is provided with a reinforcement ring 129' in those applications where sleeve 124' is a structural member. In this embodiment, the elastomeric means 122' is made up of a plurality of generally cylindrical units 123'. Each cylindrical unit has a radially extending flange 121', the plurality of flanges 121' fitting snugly in sleeve 124' and serving as the guide means in this embodiment. This elastomeric means 122', like its predecessor, is inherently unstable. The close fitting sleeve 124' provides means to stabilize the collapse of the elastomer by its piston 134'. The opposite (upper) end of sleeve 124' is closed by cylindrical collar 130' which slidingly receives piston rod 134', piston head 146' engaging the upper end of elastomeric means 122'. The majority of the length of piston rod 134' has a square configuration (FIG. 3B) which is received in a like shaped opening 135' in cylindrical collar 130'.

A cylindrical external attachment means 150' is received over the upper end of sleeve 124'. A slide bearing 152' is received by the internal periphery of attachment means 150' to facilitates relative axial movement of attachment means 150' to sleeve 124'. An axial bore 141' through piston rod 134' is threaded and receives a fastener 154'. This fastener 154' secures attachment means 150' to piston rod 134', with a cylindrical portion 137' of piston rod 134' being received in a similarly shaped recess 155'. Piston rod 134' will move concurrently with external attachment means 150' to collapse elastomeric means 122', with square shaft in square opening 135' preventing relative rotation between sleeve 124' and attachment means 150'. For appropriate applications, plug 125' can have a bore 157' that is threaded to receive an adjustment bolt 158'. Bolt 158' bears against washer 160' and by adjusting its position relative to plug 125', the amount of precompression of elastomeric means 122' can be varied. (This feature would preferably not be added to the leg prosthesis application, disclosed herein, in order to avoid user tampering which could result in personal injury.)

One potential application for this third embodiment is as a prosthetic leg. Prosthetic limbs lack some of the resiliency their natural counterparts have and make walking more difficult. By employing the cush 120' of the present invention, the resiliency provided by various components of the leg is effectively restored. In use, the cush 120' as shown in FIG. 3A will be received in adapters 162' in prosthetic foot 16' and 163' in stump cap 165'. Lower and upper ends of cush 120' are received in, for example, 31 mm adapters manufactured by Hosmer US identified by part no. 39504. It will be understood that the specified adapter is regarded as merely exemplary and that the cush 120' of the present invention could be configured to operate with other adapters, as well. In addition, the cush of the present invention is not limited to application with seat height adjusters and leg prostheses, but can be used in a variety of other applications where energy management is desired.

Various changes, alternatives and modifications will become apparent to one of ordinary skill in the art following a reading of the foregoing specification. It is intended that all such changes, alternatives and modifications as fall within the scope of the appended claims be considered part of the present invention.

What is claimed is:

1. A prosthetic suspension unit comprising:
   (a) a first member adapted to be secured to a first prosthetic member;
   (b) a stop located in the first member;
   (c) an attachment member adapted to be secured to a second prosthetic member;
   (d) a bearing member operative between the attachment member and the first member such that the attachment member may slide freely in an axial direction relative to the first member;

(e) an elastomeric energy storage element positioned within the first member and including a first portion abutting the stop; and (f) a face axially moveable with the attachment member and positioned to abut a second portion of the elastomeric energy storage element.

2. The prosthetic suspension unit according to claim 1 further comprising a first flat surface on the first member engaging a second flat surface on the attachment member wherein the attachment member is prevented from rotation relative to the first member.

3. The prosthetic suspension unit according to claim 1 wherein the stop comprises a separate plug received in the first member.

4. The prosthetic suspension unit according to claim 1 wherein the first member comprises a sleeve.

5. The prosthetic suspension unit according to claim 4 wherein the sleeve comprises a constant diameter along an entire length thereof.

6. The prosthetic suspension unit according to claim 1 wherein the elastomeric energy storage element directly contacts the stop.

7. The prosthetic suspension unit according to claim 1 wherein the elastomeric energy storage element comprises a durometer of between 50 and 80.

8. The prosthetic suspension unit according to claim 1 wherein the elastomeric energy storage element is positioned entirely within the first member.

9. The prosthetic suspension unit according to claim 1 wherein the elastomeric energy storage element comprises a plurality of units.

10. The prosthetic suspension unit according to claim 1 wherein the elastomeric energy storage element comprises a length substantially longer than a width thereof.

11. The prosthetic suspension unit according to claim 1 wherein attachment member is received over the first member.

12. The prosthetic suspension unit according to claim 1 further comprising a threaded adjustment member for adjusting an amount of precompression applied to the elastomeric energy storage member.

13. The prosthetic suspension unit according to claim 1 wherein attachment member is manufactured from a material selected from a group consisting of a urethane, natural rubber, and a plastic.

14. The prosthetic suspension unit according to claim 1 further comprising an anti-rotator member integral with the attachment member.

15. A prosthesis suspension unit comprising:

(a) a sleeve adapted to be secured to a first prosthetic member;

(b) a stop stationarily positioned in the sleeve;

(c) an attachment member adapted to be secured to a second prosthetic member;

(d) a slide bearing operative between the attachment member and the sleeve such that the attachment member may slide freely in an axial direction relative to the sleeve;

(e) an elastomeric energy storage member positioned within the sleeve, the elastomeric energy storage member having a first end abutting the stop and a length which is substantially longer than a width thereof;

(f) a face portion axially moveable with the attachment member and positioned to engage a second end of the elastomeric energy storage member; and (g) an anti-rotator including a first load bearing surface on the sleeve engaging a second load bearing surface on the attachment member and preventing relative rotation therebetween whereby the elastomeric energy storage member will provide a cushioning action to a prosthetic user.

16. A prosthesis suspension unit comprising:

(a) a sleeve attachable to a first prosthetic member;

(b) a plug positioned in the sleeve;

(c) an attachment member attachable to a second prosthetic member;

(d) a slide bearing operative between the attachment member and the sleeve such that the attachment member may slide freely in an axial direction relative to the sleeve;

(e) an elastomeric energy storage member positioned with the sleeve and including a first end adjacent to the plug;

(f) an engagement surface operative with the attachment member and positioned to move axially relative to the sleeve to engage a second end of the elastomeric energy storage member;

(g) torsional load reacting surfaces formed on the sleeve and the attachment member which engage to prevent relative rotation between the sleeve and attachment member; and (h) a threaded adjuster for precompressing the elastomeric energy storage member whereby the elastomeric energy storage member provides a cushioning action to a prosthetic user.

17. A prosthesis suspension unit attachable between first and second prosthetic members, comprising:

(a) a sleeve attachable to the first prosthetic member;

(b) a stop included in the sleeve;

(c) an attachment member attachable to the second prosthetic member;

(d) a bearing positioned between the attachment member and the sleeve such that said attachment member may move axially relative to the sleeve;

(e) an elastomeric energy storage member including a first end abutting to the stop;

(f) a surface operative with the attachment member and abutting a second end of the elastomeric energy storage member; and (g) an anti-rotator member integral with the attachment member and operative to prevent relative rotation between the attachment member and the sleeve.

18. A prosthesis suspension unit attachable between first and second prosthetic members, comprising:

(a) a sleeve of substantially constant diameter along its length attachable to the first prosthetic member;

(b) a stop included within the sleeve, (c) an attachment member attachable to the second prosthetic member, the attachment member including a cylindrical portion received over an end portion of the sleeve;

(d) a bearing allowing relative axial motion between the cylindrical portion of the attachment member and the end portion of the sleeve;

(e) an elastomer member housed within the sleeve and including a first portion abutting the stop;

(f) a contacting member axially immovable relative to the attachment member and moveable relative to the sleeve which engages a second portion of the elastomer member; and (g) an anti-rotator operative between said sleeve and said attachment member preventing relative rotation therebetween.

* * * * *